United States Patent
Eriksson (10) Patent No.: US 11,357,941 B2
(45) Date of Patent: Jun. 14, 2022

(54) BREATHING APPARATUS, METHOD OF CONTROLLING A BREATHING APPARATUS, COMPUTER PROGRAM AND COMPUTER PROGRAM PRODUCT

(71) Applicant: MAQUET CRITICAL CARE AB, Solna (SE)

(72) Inventor: Mats Eriksson, Sollentuna (SE)

(73) Assignee: MAQUET CRITICAL CARE AB, Solna (SE)

( * ) Notice: Subject to any disclaimer, the term of this patent is extended or adjusted under 35 U.S.C. 154(b) by 370 days.

(21) Appl. No.: 16/487,370

(22) PCT Filed: Mar. 7, 2017

(86) PCT No.: PCT/SE2017/050206
§ 371 (c)(1),
(2) Date: Aug. 20, 2019

(87) PCT Pub. No.: WO2018/164611
PCT Pub. Date: Sep. 13, 2018

(65) Prior Publication Data
US 2020/0054846 A1 Feb. 20, 2020

(51) Int. Cl.
*A61M 16/01* (2006.01)
*A61M 16/00* (2006.01)
*A61M 16/10* (2006.01)

(52) U.S. Cl.
CPC ........ *A61M 16/01* (2013.01); *A61M 16/0051* (2013.01); *A61M 16/0096* (2013.01);
(Continued)

(58) Field of Classification Search
CPC .............. A61M 16/01; A61M 16/0051; A61M 16/0096; A61M 16/12; A61M 16/104;
(Continued)

(56) References Cited

U.S. PATENT DOCUMENTS

| 7,242,403 B2 * | 7/2007 | Phelan | ................ | G06F 3/04847 345/440 |
| 2001/0004893 A1 * | 6/2001 | Biondi | .............. | A61M 16/0051 128/204.18 |

(Continued)

FOREIGN PATENT DOCUMENTS

| CN | 104288884 | 1/2015 |
| CN | 104471578 | 3/2015 |

(Continued)

*Primary Examiner* — Colin W Stuart
*Assistant Examiner* — Douglas Y Sul
(74) *Attorney, Agent, or Firm* — Fay Kaplun & Marcin, LLP.

(57) ABSTRACT

A breathing apparatus includes a control unit configured to control operation of the breathing apparatus based on at least a first input value and a second input value. The breathing apparatus also includes a graphical user interface connected to the control unit. The control unit is configured to display a visual output on the graphical user interface including an area defined by a first axis and a second axis. In addition, the breathing apparatus includes an input unit configured to provide selection of a portion of the area. The control unit is configured to set the first input value in response to the position of the selected portion relative the first axis and to set the second input value in response to the position of the selected portion relative the second axis.

26 Claims, 3 Drawing Sheets

(52) U.S. Cl.
CPC ........... *A61M 2016/0027* (2013.01); *A61M 2016/0039* (2013.01); *A61M 2016/0042* (2013.01); *A61M 2016/1035* (2013.01); *A61M 2205/276* (2013.01); *A61M 2205/505* (2013.01)

(58) Field of Classification Search
CPC ............ A61M 16/022; A61M 16/024; A61M 2016/1035; A61M 2205/583; A61M 2205/505; A61M 2205/276; A61M 2205/502; A61M 2205/584
See application file for complete search history.

(56) References Cited

U.S. PATENT DOCUMENTS

| | | | |
|---|---|---|---|
| 2007/0234236 A1* | 10/2007 | Champion | G06F 3/04847 715/833 |
| 2010/0011307 A1 | 1/2010 | Desfossez et al. | |
| 2011/0175728 A1 | 7/2011 | Baker, Jr. | |
| 2011/0232641 A1* | 9/2011 | Haggblom | A61M 16/205 128/204.21 |
| 2013/0133655 A1* | 5/2013 | Kimm | A61M 16/0096 128/204.23 |
| 2014/0032241 A1* | 1/2014 | Coffeng | A61B 5/0205 705/3 |
| 2014/0352693 A1* | 12/2014 | Pessala | A61M 16/18 128/203.14 |
| 2015/0193585 A1* | 7/2015 | Sunna | G06F 3/04883 345/173 |
| 2018/0001040 A1* | 1/2018 | Okita | F04B 23/02 |
| 2018/0369525 A1* | 12/2018 | Buschke | A61B 5/082 |

FOREIGN PATENT DOCUMENTS

| | | |
|---|---|---|
| EP | 2201978 | 6/2010 |
| EP | 2303372 | 4/2011 |
| WO | 2010/005763 | 1/2010 |

* cited by examiner

BREATHING APPARATUS, METHOD OF CONTROLLING A BREATHING APPARATUS, COMPUTER PROGRAM AND COMPUTER PROGRAM PRODUCT

TECHNICAL FIELD

The present invention relates to a breathing apparatus comprising a breathing circuit provided with a patient interface, wherein the breathing circuit is configured to provide an inspiratory patient gas mixture to the patient interface. The present invention further relates to a method of controlling operation of a breathing apparatus, a computer program for performing a method of controlling operation of a breathing apparatus and a computer program product for performing a method of controlling operation of a breathing apparatus.

BACKGROUND

Breathing apparatuses are used to assist patients having difficulties in breathing on their own. In order to ensure that sufficient oxygen is available in the lungs, a breathing apparatus may be used to mechanically assist or replace spontaneous breathing. A breathing apparatus works by increasing the patient's airway pressure through a patient interface, such as a mask or an endotracheal or tracheostomy tube. The increased pressure forces air to flow into the lungs.

When the breathing apparatus reduces the pressure, the elastic contraction of the chest collapses the lungs and pushes a volume of air out. The volume of air that is introduced into, and pushed out of, the lungs on each cycle is usually referred to as "tidal volume."

A breathing apparatus usually comprises one or more input units, such as knobs, buttons and/or touch sensitive screens via which a user, such as a clinical operator, may set and change various input values controlling features of the breathing apparatus. Examples of such features are concentration of an anesthetic agent, flowrate of patient gas delivered to the patient interface, respiratory frequency of patient gas delivered to the patient interface, tidal volume of patient gas delivered to the patient interface, etc. The document US20140352693 A1 relates to a breathing apparatus comprising an input unit in the form of a touch screen.

Operators of breathing apparatuses usually spend valuable time adjusting and checking operation of the breathing apparatus in parallel with a multitude of other time-consuming and complex tasks. An incorrect setting of a control feature may have negative consequences, especially for a patient being anesthetized. Therefore, it is an advantage if a breathing apparatus is easy to control in an intuitive manner.

SUMMARY

The present invention relates to a breathing apparatus with a facilitated control.

In particular, the present invention relates to a breathing apparatus comprising a breathing circuit provided with a patient interface. The breathing circuit is configured to provide an inspiratory patient gas mixture to the patient interface. The breathing apparatus comprises a control unit configured to control operation of the breathing apparatus based on at least a first input value and a second input value. The breathing apparatus comprises a graphical user interface connected to the control unit. The control unit is configured to display a visual output on the graphical user interface comprising an area defined by a first axis and a second axis. The first axis represents values of the first input value and the second axis represents values of the second input value. The breathing apparatus further comprises an input unit configured to provide selection of a portion of the area, wherein the control unit is configured to set the first input value in response to the position of the selected portion relative the first axis and to set the second input value in response to the position of the selected portion relative the second axis.

Accordingly, a user of the breathing apparatus may set the first input value, as well as the second input value, simply by selecting a portion of the area using the input unit. Thus, a facilitated control of a breathing apparatus is provided.

Further, since the user of the breathing apparatus may set the first input value, as well as the second input value, simply by selecting a portion of the area using the input unit, a user-friendly breathing apparatus is provided in which the risk of an incorrect setting of the first and second input values is reduced. As a result, patient safety is improved. In addition, conditions are provided for assisting a user in the selection of the first and second input values by improving the understanding of how the first and second input values interact and influence each other. Thereby, patient safety can be further improved.

Optionally, the area comprises at least a first sub-area, wherein the first sub-area represents a primary operational area comprising selectable portions at positions relative the first and second axis representative of first and second input values within the primary operational area. Thereby, a user may select a portion within the at least first sub-area and consequently select first and second input values within the primary operational area in an intuitive manner. Accordingly, a further facilitated control of a breathing apparatus is provided which may further improve patient safety.

Optionally, the primary operational area is a preferred operational area. Thereby, a user may select a portion within the preferred operational area in an intuitive manner. As a result, control of the breathing apparatus is further facilitated and the patient safety is further improved.

Optionally, the area comprises at least a second sub-area, wherein the second sub-area represents a secondary operational area comprising portions at positions relative the first and the second axis representative of the first and second input values, within the secondary operational area. Thereby, a user may select a portion within the second sub-area and consequently select first and second input values within the secondary operational area in an intuitive manner. Accordingly, control of the breathing apparatus is further facilitated and the patient safety is further improved.

Optionally, the secondary operational area is a non-preferred operational area. Since the non-preferred operational area, according to these embodiments, is represented by second sub-area, a user may discern the non-preferred operational area in the visual output on the graphical user interface and may thereby be prevented from unintentionally selecting a portion within the non-preferred operational area. As a result, a further facilitated control of the breathing apparatus is provided and the patient safety is further improved.

Optionally, the control unit is configured to prevent unintended selection of portions within the second sub-area by outputting a notification if a portion is selected within the second sub-area. Thereby, a user is further prevented from unintentionally selecting a portion within the second sub-area. As a result, control of the breathing apparatus is further facilitated and the patient safety is further improved.

Optionally, the control unit is configured to prevent unintended selection of portions within the second sub-area by requiring an additional control manoeuvre to be performed on the input unit to allow a selection of a portion within the second sub-area. Thereby, a user is further prevented from unintentionally selecting a portion within the second sub-area. As a result, control of the breathing apparatus is further facilitated and the patient safety is even further improved.

Optionally, the second sub-area is determined on the basis of individual properties and/or characteristics of a patient. Thereby, a second sub-area is provided being determined on the basis of individual properties and/or characteristics of a patient which further facilitates control of the breathing apparatus and improves the patient safety.

Optionally, the control unit is configured to display a symbol in the area at a position relative the first and second axis representative of a current first input value and current second input value used to control operation of the breathing apparatus. Thereby, a user can in an intuitive manner detect and verify current first and second input values currently used to control operation of the breathing apparatus. As a result, control of the breathing apparatus is further facilitated and the patient safety is even further improved.

Optionally, the input unit is configured to provide selection of the portion of the area by allowing a user to perform a drag and drop control operation of the symbol in the area. Thereby, a user can in an intuitive manner detect and verify current first and second input values used to control operation of the breathing apparatus, and may change the first and second input values used in a simple and intuitive manner by performing drag and drop control operation of the symbol. As a result, control of the breathing apparatus is even further facilitated and the patient safety is even further improved since the risk of an incorrect setting of the first and second input values is further reduced.

Optionally, the graphical user interface and the input unit form part of a touch sensitive screen. Thereby, a breathing apparatus is provided in which a user may set the current first and second input values simply by selecting of a portion of the area using a finger. As a result, control of the breathing apparatus is further facilitated and the patient safety is thereby even further improved.

Optionally, the breathing apparatus is an anaesthetic breathing apparatus. In an anaesthetic breathing apparatus, it is even more important that the breathing apparatus can be controlled in a simple and intuitive manner since incorrect setting of input values may have negative consequences for a patient being anesthetized. However, as shown above, in the breathing apparatus provided, a user may set the first input value as well as the second input value simply by selecting a portion of the area using the input unit. Thus, an anaesthetic breathing apparatus is provided being easy to control in an intuitive manner. Further, since the user of the breathing apparatus may set the first input value, as well as the second input value, simply by selecting a portion of the area using the input unit, the risk of incorrect setting of the first and second input values is reduced. Thus, an anaesthetic breathing apparatus is provided offering a facilitated control thereof as well as an improved safety for a patient.

Optionally, the first input value is representative of a concentration of an anesthetic agent and the second input value is representative of a flowrate of patient gas delivered to the patient interface. Thereby, a user may control and adjust the concentration of an anesthetic agent, as well as the flowrate of patient gas delivered to the patient interface, simply by selecting a portion of the area using the input unit.

Optionally, the first input value is representative of a concentration of an anesthetic agent and the second input value is representative of a rate of change of the concentration of the anesthetic agent. Thereby, a user may control and adjust the concentration of an anesthetic agent, as well as the rate of change of the concentration of the anesthetic agent, simply by selecting a portion of the area using the input unit.

Optionally, the control unit is configured to control operation of the breathing apparatus in a high frequency ventilation mode based on at least the first and second input values, wherein the first input value is representative of a respiratory frequency delivered to the patient interface and the second input value is representative a tidal volume of gas delivered to the patient interface.

Thereby, a user may control and adjust the respiratory frequency of patient gas delivered to the patient interface and the tidal volume of patient gas delivered to the patient interface, simply by selecting a portion of the area using the input unit.

Optionally, the second input value is representative of a rate of change of the first input value. Thereby, a user may control and adjust a certain control feature as well as a rate of change of the certain control feature simply by selecting a portion of the area using the input unit.

Optionally, the first input value is representative of a concentration of fresh gas. Thereby, a user may control and adjust the concentration of fresh gas simply by selecting a portion of the area using the input unit.

Optionally, the first input value is independent from the second input value. Thereby, a user may control and adjust two different control features being independent from each other simply by selecting a portion of the area using the input unit.

Furthermore, the present invention relates to a method of controlling operation of a breathing apparatus comprising a breathing circuit provided with a patient interface, wherein the breathing circuit is configured to provide an inspiratory patient gas mixture to the patient interface, wherein the breathing apparatus comprises a control unit, a graphical user interface connected to the control unit, and an input unit, wherein the method comprises:

displaying a visual output on the graphical user interface comprising an area defined by a first axis and a second axis, using the control unit, wherein the first axis represents values of a first input value and the second axis represents values of a second input value,
 employing the input unit to select a portion of the area,
 setting the first input value in response to the position of the selected portion relative the first axis,
 setting the second input value in response to a position of the selected portion relative the second axis, and
 controlling operation of the breathing apparatus based on the first input value and the second input value, using the control unit.

Since the method comprises the steps of setting the first input value in response to the position of the selected portion relative the first axis, and setting the second input value in response to a position of the selected portion relative the second axis, a user of the breathing apparatus may set the first input value, as well as the second input value, simply by selecting a portion of the area using the input unit. Thus, a facilitated control of a breathing apparatus is provided.

Further, since the user of the breathing apparatus may set the first input value, as well as the second input value, simply by selecting a portion of the area using the input unit, a user-friendly method of controlling operation of a breathing apparatus is provided in which the risk of incorrect setting of the first and second input values is reduced. Thereby, patient safety is improved.

Optionally, the method further comprises:
displaying the visual output on the graphical user interface such that the area comprises at least a first sub-area, using the control unit, wherein the first sub-area, represents a primary operational area comprising selectable portions at positions relative the first and second axis representative of first and second input values, within the primary operational area.

Thereby, a method is provided in which a user may select a portion within the at least first sub-area and consequently select first and second input values within the primary operational area in an intuitive manner. Accordingly, a method further facilitating control of the breathing apparatus is provided which also may further improve patient safety.

Optionally, the method further comprises:
displaying the visual output on the graphical user interface such that the area comprises at least a second sub-area, using the control unit, wherein the second sub-area represents a secondary operational area comprising portions at positions relative the first and the second axis representative the first and second input values, within the secondary operational area.

Thereby, a method is provided in which a user may select a portion within the second sub-area and consequently select first and second input values within the secondary operational area in an intuitive manner. Accordingly, a method is provided further facilitating control of the breathing apparatus and further improving the patient safety.

Optionally, the method further comprises:
preventing unintended selection of portions within the second sub-area by outputting a notification if a portion is selected within the second sub-area, using the control unit.

Thereby, a method is provided in which a user is further prevented from unintentionally selecting a portion within the second sub-area. As a result, a method is provided further facilitating control of the breathing apparatus and further improving the patient safety.

Optionally, the method further comprises:
preventing unintended selection of portions within the second sub-area by requiring an additional control manoeuvre to be performed on the input unit to allow a selection of a portion within the second sub-area, using the control unit.

Thereby, a method is provided in which a user is further prevented from unintentionally selecting a portion within the second sub-area. As a result, a method is provided further facilitating control of the breathing apparatus and further improving the patient safety.

Optionally, the method further comprises:
determining the second sub-area on the basis of individual properties and/or characteristics of a patient.

Thereby, a method is provided in which the second sub-area is determined on the basis of individual properties and/or characteristics of a patient which further facilitates control of the breathing apparatus and improves the patient safety.

Optionally, the method further comprises:
displaying a symbol on the graphical user interface, using the control unit, in the area at a position relative the first and second axis representative of a current first input value and current second input value used to control operation of the breathing apparatus.

Thereby, a method is provided in which a user can in an intuitive manner detect and verify current first and second input values used to control operation of the breathing apparatus. As a result, a method is provided further facilitating control of the breathing apparatus and even further improving the patient safety.

Optionally, the method further comprises:
providing selection of the portion of the area by allowing a user to perform a drag and drop control operation of the symbol in the area, using the input unit.

Thereby, a method is provided in which a user can in an intuitive manner detect and verify current first and second input values used to control operation of the breathing apparatus, and may change the first and second input values used in a simple and intuitive manner by performing drag and drop control operation of the symbol. As a result, a method is provided further facilitating control of the breathing apparatus and even further improving the patient safety, since the risk of an incorrect setting of the first and second input values is further reduced.

In addition, the present invention relates to a computer program for performing a method of controlling operation of a breathing apparatus, wherein the computer program comprises computer readable code embedded in a control unit of the breathing apparatus and configured to cause the control unit to operate the breathing apparatus so as to perform the method according to some embodiments of above. Accordingly, the computer program comprises computer readable code configured to cause a control unit of a breathing apparatus to perform the method which facilitates control of a breathing apparatus.

Thus, a computer program is provided which facilitates control of a breathing apparatus.

Also, the present invention relates to a computer program product for performing a method of controlling operation of a breathing apparatus, wherein the computer program product comprises computer readable code embedded in a control unit of the breathing apparatus and configured to cause the control unit to operate the breathing apparatus so as to perform the method according to some embodiments of above. Accordingly, the computer program product comprises computer readable code configured to cause a control unit of a breathing apparatus to perform the method which facilitates control of a breathing apparatus.

Thus, a computer program product is provided which facilitates control of a breathing apparatus.

Further features of, and advantages with, the present invention will become apparent when studying the appended claims and the following detailed description.

BRIEF DESCRIPTION OF THE DRAWINGS

Various aspects of the invention, including its particular features and advantages, will be readily understood from the example embodiments discussed in the following detailed description and the accompanying drawings, in which.

DETAILED DESCRIPTION

Aspects of the present invention will now be described more fully. Like numbers refer to like elements throughout.

Well-known functions or constructions will not necessarily be described in detail for brevity and/or clarity.

Figure 1:
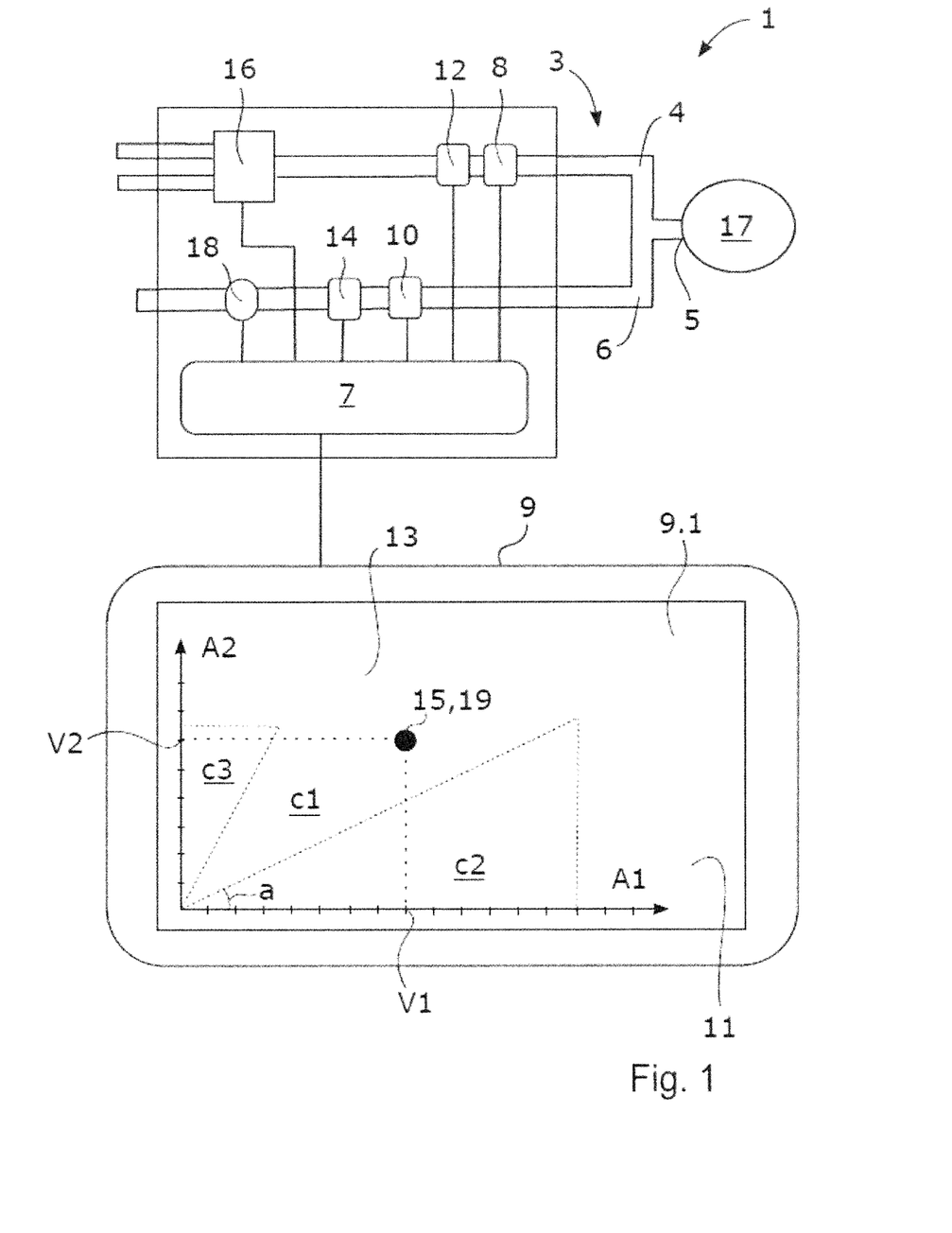
FIG. 1 illustrates a breathing apparatus, according to some embodiments of this disclosure.

FIG. 1 illustrates a breathing apparatus 1 comprising a breathing circuit 3 provided with a patient interface 5, wherein the breathing circuit 3 is configured to provide an inspiratory patient gas mixture to the patient interface 5. The patient interface 5 may comprise a mask, endotracheal tube, tracheostomy tube, or similar. The breathing apparatus 1 comprises a control unit 7 configured to control operation of the breathing apparatus 1 based on at least a first input value V1 and a second input value V2. The breathing apparatus 1 comprises a graphical user interface 9 connected to the control unit 7. The control unit 7 is configured to display a visual output 11 on the graphical user interface 9 comprising an area 13 defined by a first axis A1 and a second axis A2. The first axis A1 represents values of the first input value V1 and the second axis A2 represents values of the second input value V2. The breathing apparatus 1 further comprises an input unit 9.1 configured to provide selection of a portion 15 of the area 13. In the illustrated embodiments, the graphical user interface 9 and the input unit 9.1 form part of a touch sensitive screen. In further embodiments, the graphical user interface 9 may comprise a separate screen and the input unit may comprise a mouse, a trackball, or similar, configured to provide selection of a portion 15 of the area 13. The control unit 7 is configured to set the first input value V1 in response to the position of the selected portion 15 relative the first axis A1, and to set the second input value V2 in response to the position of the selected portion 15 relative the second axis A2.

Thereby, a user of the breathing apparatus 1 may set and change the first input value V1 as well as the second input value V2 simply by selecting a portion 15 of the area 13, using the input unit 9.1. In addition, conditions are provided for assisting a user in the selection of the first and second input values V1, V2 by improving the understanding of how the first and second input values V1, V2 interact and influence each other, as is further explained below.

In the illustrated embodiments, the area 13 comprises a first sub-area c1. The first sub-area c1 represents a primary operational area comprising selectable portions at positions relative the first and second axis A1, A2 representative of first and second input values V1, V2 within the primary operational area. The primary operational area may be a preferred operational area. A preferred operational area may, for example, encompass an area in which operation of the breathing apparatus 1 is expected to provide optimal therapeutic effect, whether with respect to respiratory support or anaesthetic administration, or both, while minimizing complications of therapy. The preferred operational area may also encompass an area in which an anaesthetic agent is used in an efficient manner regarding consumption rate of the anaesthetic agent. The primary operational area may represent certain operational conditions of control features such as concentration of an anesthetic agent, flowrate of gas delivered to the patient interface, respiratory rate, respiratory frequency of gas delivered to the patient interface, respiratory amplitude of gas delivered to the patient interface, tidal volume delivered to the patient interface, High Frequency Oscillation (HFO) frequency/amplitude, etc. The first sub-area c1 may represent how a combined setting of the first and second input values V1, V2 affects the ventilation of the patient 17.

In the illustrated embodiments, the area 13 further comprises a second sub-area c2, wherein the second sub-area c2 represents a secondary operational area comprising portions at positions relative the first and the second axis A1, A2 representative of the first and second input values V1, V2 within the secondary operational area. The secondary operational area may be a non-preferred operational area and may represent certain operational conditions of control features such as concentration of an anesthetic agent, flowrate of gas delivered to the patient interface, respiratory rate, respiratory frequency of gas delivered to the patient interface, respiratory amplitude of gas delivered to the patient interface, tidal volume delivered to the patient interface, High Frequency Oscillation (HFO) frequency/amplitude, etc. A non-preferred operational area may, for example, encompass an area in which the therapeutic effect of operating the breathing apparatus 1 under such conditions is expected, based on normalized data, to be less effective than operation of the breathing apparatus 1 under conditions corresponding to the primary operational area. The accepted but non-preferred operational area may also encompass an area in which an anaesthetic agent is used in a less efficient manner regarding consumption rate of the anaesthetic agent In the illustrated embodiments, the area 13 further comprises a third sub-area c3, wherein the third sub-area c3 represents a third operational area comprising portions at positions relative the first and the second axis A1, A2 representative of the first and second input values V1, V2 within the third operational area. The third operational area may be an operational area with certain operational conditions such as for example a rapid rate of change of the concentration of the anesthetic agent, concentration of an anesthetic agent, flowrate of gas delivered to the patient interface, respiratory rate, respiratory frequency of gas delivered to the patient interface, respiratory amplitude of gas delivered to the patient interface, tidal volume delivered to the patient interface, High Frequency Oscillation (HFO) frequency/amplitude, etc. The third operational area may, according to some embodiments, be an operational area in which selection of a portion is not allowed, for example where the operation of the breathing apparatus with first and/or second input values V1, V2 within the third operational area are expected to result in an unacceptable risk of complication to the patient and/or an unacceptable risk that therapy administered by the breathing apparatus, whether respiratory support and/or anaesthesia, will not be clinically effective. Further, the third operational area may be an operational area in which control needs to be prohibited based on expected lack of therapeutic effectiveness and/or substantially higher unacceptable complication rates based on previously obtained knowledge regarding appropriate control of a breathing apparatus, and regardless of whether the lung is healthy or diseased. In further embodiments, the third operational area may be an operational area in which an anaesthetic agent is used sparingly, as is further explained below.

The first, the second and/or the third sub-area c1, c2, c3 may be provided with different colours, patterns and/or contrasts facilitating discernment between the respective sub-area c1, c2, c3. The control unit 7 may be configured to display explanatory text in the visual output 11 on the graphical user interface 9 indicating the differences between the first, the second and/or the third sub-area c1, c2, c3 regarding operation characteristics of the breathing apparatus 1. Further, the control unit 7 may be configured to display explanatory text in the visual output 11 on the graphical user interface 9 indicating how a combined setting of the first and second input values V1, V2 within one or more of the first, the second and/or the third sub-area c1, c2, c3 affects the ventilation of the patient 17. For example, the control unit 7 may be configured to display explanatory text indicating that the first sub-area c1 is an area in which operation of the breathing apparatus 1 is expected to provide optimal therapeutic effect, whether with respect to respiratory support or anaesthetic administration, or both, while minimizing complications of therapy. In further embodiments, the control unit 7 may be configured to display explanatory text indicating that the first sub-area c1 is an area in which an anaesthetic agent is used in an efficient manner regarding consumption rate of the anaesthetic agent.

Further, the control unit 7 may be configured to display explanatory text indicating that the second sub-area c2 is a non-preferred operational area. In further embodiments, the control unit 7 may be configured to display explanatory text indicating that the second sub-area c2 encompass an area in which the therapeutic effect of operating the breathing apparatus 1 under such conditions is expected, based on normalized data, to be less effective than operation of the breathing apparatus 1 under conditions corresponding to the primary operational area. In still further embodiments, the control unit 7 may be configured to display explanatory text indicating that the second sub-area c2 encompass an area in which an anaesthetic agent is used in a less efficient manner regarding consumption rate of the anaesthetic agent.

Further, the control unit 7 may be configured to display explanatory text indicating that the third sub-area c3 is an operational area in which selection of a portion is not allowed. According to further embodiments, the control unit 7 may be configured to display explanatory text indicating that operation of the breathing apparatus with first and/or second input values V1, V2 within the third sub-area c3 is expected to result in an unacceptable risk of complication to the patient and/or an unacceptable risk that therapy administered by the breathing apparatus, whether respiratory support and/or anaesthesia, will not be clinically effective. Further, the control unit 7 may be configured to display explanatory text indicating that the third sub-area c3 is an operational area in which control needs to be prohibited based on expected lack of therapeutic effectiveness and/or substantially higher unacceptable complication rates based on previously obtained knowledge regarding appropriate control of a breathing apparatus. In further embodiments, the control unit 7 may be configured to display explanatory text indicating that the third sub-area c3 is an operational area in which the anaesthetic agent is used sparingly, as will be further explained below. Due to the display of explanatory text in the visual output 11 on the graphical user interface 9 as described above, a user may easily distinguish the respective sub-area c1, c2, c3 and be provided with information indicating how selection of portions within the first, the second and/or the third sub-area c1, c2, c3 affects operation of the breathing apparatus 1. As a result, the user is assisted in making a conscious selection of a portion within one of the respective sub-area c1, c2, c3 to set the first and second input values V1, V2 appropriate for a current situation.

Further, the control unit may be configured to display the explanatory text anywhere within area 13 or sub-area specific information within each respective sub-area c1, c2, c3. The control unit may also be configured to display additional explanatory information upon touching anywhere within or adjacent the area of the explanatory text in area 13 or upon touching anywhere within the respective sub area c1, c2, c3, including the area of the already displayed explanatory information. Such additional explanatory information may relate to further detailed information regarding advantages/disadvantages of the chosen sub area.

The control unit 7 may be configured to prevent unintended selection of portions within the second sub-area c2 by outputting a notification if a portion is selected within the second sub-area c2. The notification may be outputted as a visual notification on graphical user interface 9. The notification may comprise a message and/or a contextual help outputted if a portion is selected within the second sub-area c2. The message and/or a contextual help may comprise additional information that the user can access for example by clicking on the message to find out why an area is non-preferred or non-allowable. As an alternative, or in addition, the notification may be outputted as an audio notification by a speaker. By outputting a notification if a portion is selected within the second sub-area c2, a user is prevented from unintentionally selecting a portion within the second sub-area c2.

Further, the control unit 7 may be configured to prevent unintended selection of portions within the second sub-area c2 by requiring an additional control manoeuvre to be performed on the input unit 9.1 to allow a selection of a portion within the second sub-area c2. The additional control manoeuvre to be performed on the input unit 9.1 may, for example, comprise a swipe movement on the input unit 9.1 or a clicking of a box outputted on the graphical user interface 9. In other words, the additional control manoeuver provides an override that a clinician may employ if it is determined based on the clinician's judgment that operation of the breathing apparatus outside of predicted norms is warranted.

One or more of the first, the second and the third sub-areas c1, c2, c3 may comprise contextual information at a portion thereof, which may be expanded for example by clicking or performing a tap and hold gesture. Thereby, a user can be further guided in the settings and in the control of the breathing apparatus 1.

According to further embodiments, the control unit 7 may be configured to not allow selection of a portion within the second sub-area c2, and may in response to an attempt to a selection of such portion output a notification informing a user that the selection is not allowed. In this way, the breathing apparatus may be controlled to prevent clinically unacceptable operation of the breathing apparatus According to some embodiments, the first, the second and the third sub-areas c1, c2, c3 may be determined on the basis of individual properties and/or characteristics of a patient 17. That is, a user of breathing apparatus 1 may, for example via the input unit 9.1, input individual properties and/or characteristics of the patient 17 such as weight, length, age, body mass index, etc., wherein the control unit 7 is configured to, on the basis of the inputted individual properties and/or characteristics determine one or more of the first, the second and the third sub-areas c1, c2, c3, i.e. determine the size and/or shape of one or more of the first, the second and the third sub-areas c1, c2, c3. Thereby, first, second and third sub-areas c1, c2, c3 can be provided in a customized manner adapted to the patient 17. In the illustrated example embodiments of FIG. 1, the angle a defines the size of the second sub-area c2. The angle a may for example be set in dependence of length and weight of a patient 17 and may therefore define a non-preferred operational area for the current patient 17. Generally, the basic understanding among users of how different settings interact can be considered as low. However, since the breathing apparatus 1 may provide the different sub-areas c1, c2, c3, a user can be guided in the settings and in the control of the breathing apparatus 1 and the user can be guided in the process of understanding how the first and second input values V1, V2 interact and influence each other to be able to achieve a proper combined setting of the first and second input values V1, V2.

According to the illustrated embodiments, the control unit 7 is configured to display a symbol 19 on the graphical user interface 9 in the area 13 at a position relative the first and second axis A1, A2 representative of a current first input value V1 and current second input value V2 used to control operation of the breathing apparatus 1. Thereby, a user may in an intuitive manner detect and verify current first and second input values V1, V2 used to control operation of the breathing apparatus 1. Further, in the illustrated embodiments, the input unit 9.1 is configured to provide selection of the portion 15 of the area 13 by allowing a user to perform a drag and drop control operation of the symbol 19 in the area 13. Thereby, a user may set and adjust the first and second input values V1, V2 in a simple and intuitive manner by performing drag and drop control operation of the symbol 19.

According to some embodiments of this disclosure, the breathing apparatus 1 is an anaesthetic breathing apparatus. In such embodiments, the first input value V1 may be representative of a concentration of an anesthetic agent and the second input value V2 may be representative of a flowrate of patient gas delivered to the patient interface 5. Generally, the basic understanding among users of the interaction between the concentration of an anesthetic agent and the flowrate of patient gas delivered to the patient interface can be considered low. This since the amount of anesthetic agent delivered to the patient is affected by the concentration of the anesthetic agent as well as by the flowrate of patient gas delivered to the patient interface.

However, according to these embodiments, a user may set and control the concentration of the anesthetic agent, as well as the flowrate of patient gas delivered to the patient interface 5, in a more intuitive manner simply by selecting a portion 15 of the area 13 using the input unit 9.1, since the user is assisted in the understanding of how the first and second input values interact and influence each other. In these embodiments, the second sub-area c2 may represent a secondary operational area in which a fast increase is obtained of the concentration of an anesthetic agent. The third sub-area c3 may represent a third operational area in which the anesthetic agent is used sparingly. Anesthetic agents used in breathing apparatuses, such as Desflurane, Isoflurane, Sevoflurane and Nitrous Oxide, are usually expensive and may be potentially harmful for the environment. However, in these embodiments, the user is assisted in the decision making to be able to control the breathing apparatus 1 to deliver an adequate amount of anesthetic agent to the patient 17.

In further embodiments of this disclosure, the first input value V1 may be representative of a concentration of an anesthetic agent and the second input value V2 may be representative of a rate of change of the concentration of the anesthetic agent. Accordingly, in such embodiments, a user may set and control the concentration of the anesthetic agent as well as the rate of change of the concentration of the anesthetic agent in a more intuitive manner simply by selecting a portion 15 of the area 13 using the input unit 9.1.

According to further embodiments of this disclosure, the control unit 7 is configured to control operation of the breathing apparatus 1 in a high frequency ventilation mode based on at least the first and second input values V1, V2, wherein the first input value V1 is representative of a respiratory frequency delivered to the patient interface 5 and the second input value V2 is representative a tidal volume of gas delivered to the patient interface 5. Accordingly, in such embodiments, a user may set and control the respiratory frequency of delivered to the patient interface 5 and the tidal volume of patient gas delivered to the patient interface 5 in a more intuitive manner simply by selecting a portion 15 of the area 13, using the input unit 9.1.

According to some embodiments, the second input value V2 is representative of a rate of change of the first input value V1. Thereby, a user may control and adjust a certain control feature as well as a rate of change of the certain control feature simply by selecting a portion 15 of the area 13 using the input unit 9.1.

According to some embodiments, the first input value V1 is representative of a concentration of fresh gas. The expression "fresh gas" is intended to encompass a mixture of oxygen and anesthetic agent. Thereby, a user may control and adjust the concentration of fresh gas simply by selecting a portion 15 of the area 13 using the input unit 9.1. In addition, in embodiments in which the second input value V2 is representative of a rate of change of the first input value V1 and the first input value V1 is representative of a concentration of fresh gas, a user may control and adjust the concentration of fresh gas, as well as a rate of change of the concentration of fresh gas, simply by selecting a portion 15 of the area 13, using the input unit 9.1.

According to some embodiments of this disclosure, the first input value V1 is independent from the second input value V2. Thereby, a user may control and adjust two different control features that constitute independent parameters, distinct from each other in cause and effect, simply by selecting a portion 15 of the area 13 using the input unit 9.1.

According to some embodiments, the first input value V1 and the second input value V2 are physical parameters controllable by the breathing apparatus. Such physical parameters, controllable by the breathing apparatus, may for example comprise concentration of an anesthetic agent, flowrate of gas delivered to the patient interface, pressure of gas delivered to the patient interface, respiratory rate, respiratory frequency of gas delivered to the patient interface, respiratory amplitude of gas delivered to the patient interface, tidal volume delivered to the patient interface, High Frequency Oscillation (HFO) frequency/amplitude, etc. According to some embodiments, the first input value V1 and the second input value V2 are representative of parameters not comprising time per se or time periods, for example time periods measured in seconds, minutes, or equivalents thereof.

According to the embodiments illustrated in FIG. 1, the breathing apparatus 1 comprises an inspiratory channel 4 and an expiratory channel 6. The breathing apparatus 1 illustrated in FIG. 1 further comprises an inspiratory channel flow meter 8, an expiratory channel flow meter 10, an inspiratory channel pressure gauge 12, an expiratory channel pressure gauge 14, an inspiratory channel gas regulator 16 and an expiratory channel gas flow regulator 18. All these components are connected to the control unit 7. In the illustrated example embodiments, the control unit 7 may control operation of the breathing apparatus 1 based on the first input value V1 and the second input value V2 as well as values from the inspiratory channel flow meter 8, the expiratory channel flow meter 10, the inspiratory channel pressure gauge 12 and the expiratory channel pressure gauge 14. The control of operation of the breathing apparatus 1 in the illustrated embodiments may encompass control of the inspiratory channel gas regulator 16 and the expiratory channel gas flow regulator 18.

The breathing apparatus 1 illustrated in FIG. 1 is solely an example embodiment of a breathing apparatus 1. The breathing apparatus 1 may comprise other components such as a blower, a fan, one or more check valves, one or more valves for controlling flow in the inspiratory channel, and/or expiratory channel, a closed breathing circuit, a pressurized oxygen source, oxygen air or other gas sources, an oxygen valve configured to selectively deliver a flow of oxygen from a pressurized oxygen source to the inspiratory channel 4, etc. The control operation of the breathing apparatus 1 may thus encompass control of one or more of such components.

Figure 2:
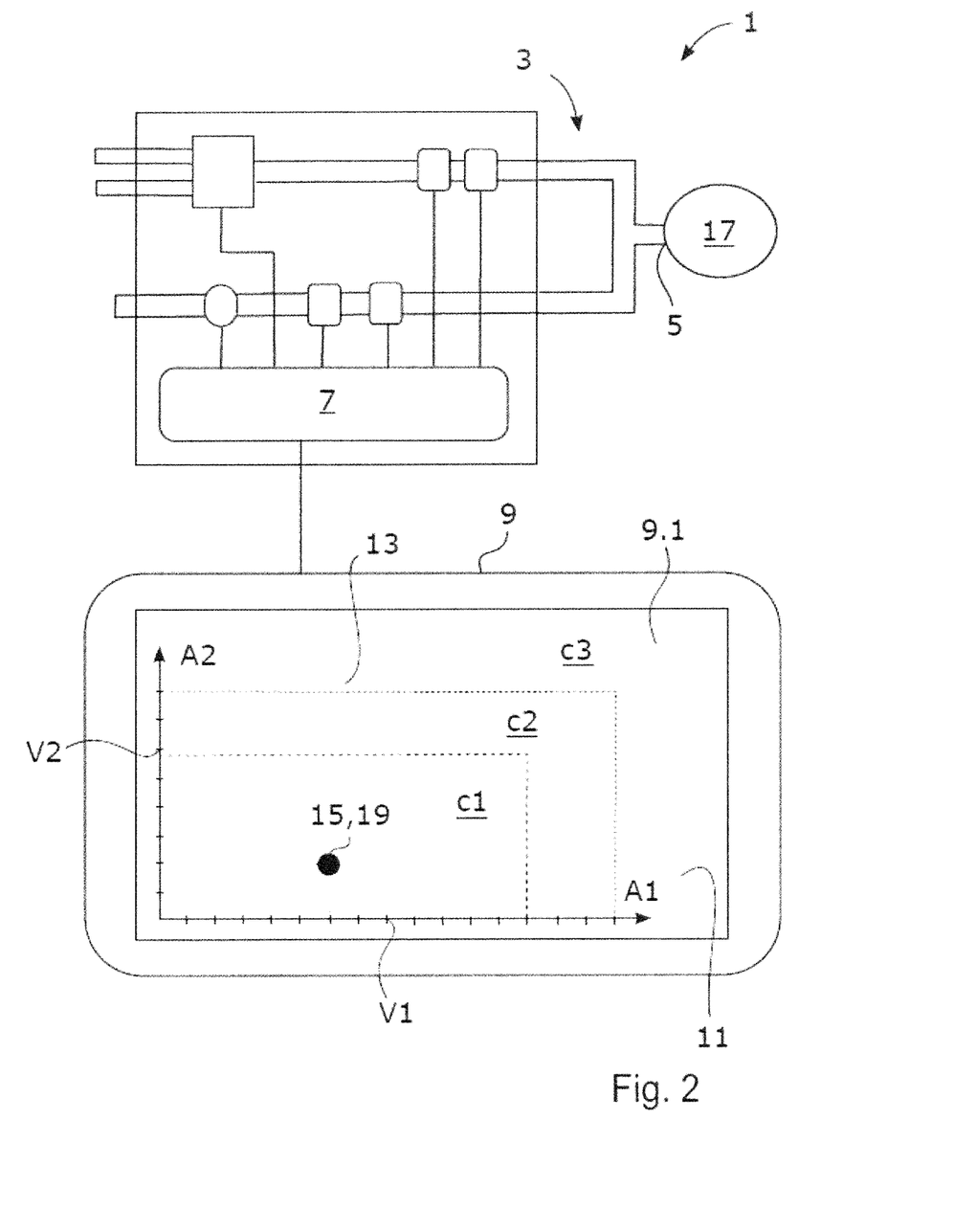
FIG. 2 illustrates a breathing apparatus, according to some further embodiments of this disclosure.

FIG. 2 illustrates a breathing apparatus 1 according to some further embodiments of this disclosure. The breathing apparatus 1 illustrated in FIG. 2 comprises the corresponding features as the breathing apparatus 1 illustrated in FIG. 1, except the outputting of the visual output 11 on the graphical user interface 9. In FIG. 2, the first sub-area c1 of the area 13 represents a primary operational area comprising selectable portions at positions relative the first and second axis A1, A2 representative of first and second input values V1, V2 within the primary operational area. In the illustrated embodiments, the primary operational area is a preferred operational area. The preferred operational area may, for example, encompass an area in which operation of the breathing apparatus 1 is expected to provide optimal therapeutic effect, whether with respect to respiratory support or anaesthetic administration, or both, while minimizing complications of therapy. The preferred operational area may also encompass an area in which an anaesthetic agent is used in an efficient manner regarding consumption rate of the anaesthetic agent.

The area 13 further comprises a second sub-area c2, wherein the second sub-area c2 represents a secondary operational area comprising portions at positions relative the first and the second axis A1, A2 representative of the first and second input values V1, V2 within the secondary operational area. In the illustrated embodiments, the secondary operational area is an accepted but non-preferred operational area. The accepted but non-preferred operational area may, for example, encompass an area in which the therapeutic effect of operating the breathing apparatus 1 under such conditions is expected, based on normalized data, to be less effective than operation of the breathing apparatus 1 under conditions corresponding to the primary operational area. The accepted but non-preferred operational area may also encompass an area in which an anaesthetic agent is used in a less efficient manner regarding consumption rate of the anaesthetic agent. If a portion 15 of the area 13 is selected within the second sub-area c2, the control unit 7 may be configured to prevent unintended selection of portions within the second sub-area c2 by outputting a notification. Further, the control unit 7 may be configured to prevent unintended selection of portions within the second sub-area c2 by requiring an additional control manoeuvre, i.e. an operational override, to be performed on the input unit 9.1 to allow a selection of a portion within the second sub-area c2.

The area 13 further comprises a third sub-area c3. In these embodiments, the third sub-area c3 is a non-allowed operational area, and the control unit 7 is configured to not allow a selection of a portion within the third sub-area c3. The non-allowed operational area may encompass an area in which, based on normalized data, operational of the breathing apparatus 1 under these conditions is associated with an unacceptable risk of complications and/or a clinically unacceptable therapeutic deviation. The control unit 7 may be configured to output a notification to a user if the user tries to select a portion of the area 13 within the third sub-area c3. The first, the second and/or the third sub-areas c1, c2, c3 may, also according to these embodiments, be determined on the basis of inputted individual properties and/or characteristics of a patient 17.

Figure 3:
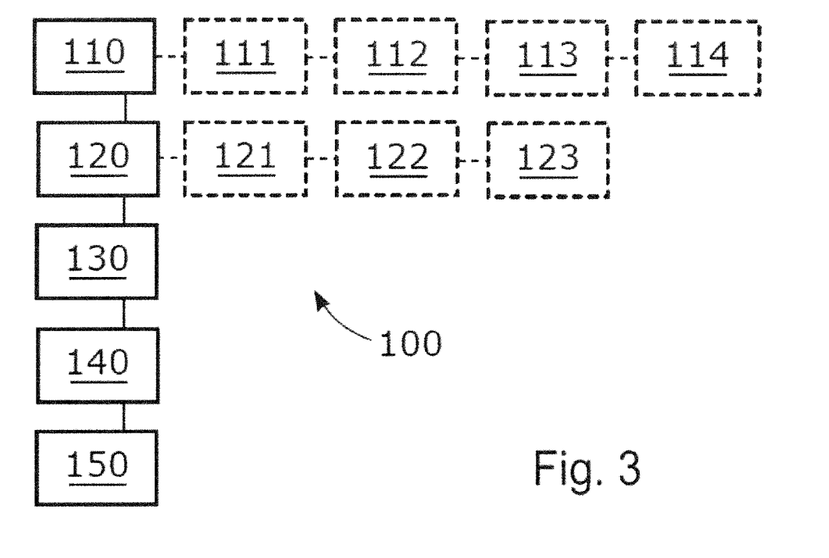
FIG. 3 illustrates a method of controlling operation of a breathing apparatus.

FIG. 3 illustrates a method 100 of controlling operation of a breathing apparatus 1. The method 100 may be performed on a breathing apparatus 1 as illustrated in FIG. 1 or FIG. 2. Therefore, below, reference is made to FIG. 3 as well as to FIG. 1 and FIG. 2. The method 100 is a method 100 of controlling operation of a breathing apparatus 1 comprising a breathing circuit 3 provided with a patient interface 5, wherein the breathing circuit 3 is configured to provide an inspiratory patient gas mixture to the patient interface 5, wherein the breathing apparatus 1 comprises a control unit 7, a graphical user interface 9 connected to the control unit 7, and an input unit 9.1. The method 100 comprises:

displaying 110 a visual output 11 on the graphical user interface 9 comprising an area 13 defined by a first axis A1 and a second axis A2, using the control unit 7, wherein the first axis A1 represents values of a first input value V1 and the second axis A2 represents values of a second input value V2, employing 120 the input unit 9.1 to select a portion 15 of the area 13, setting 130 the first input value V1 in response to the position of the selected portion 15 relative the first axis A1, setting 140 the second input value V2 in response to a position of the selected portion 15 relative the second axis A2, and controlling 150 operation of the breathing apparatus 1 based on the first input value V1 and the second input value V2, using the control unit 7.

As illustrated in FIG. 3, the method 100 may further comprise:

displaying 111 the visual output 11 on the graphical user interface 9 such that the area 13 comprises at least a first sub-area c1, c3, using the control unit 7, wherein the first sub-area c1, c3 represents a primary operational area comprising selectable portions at positions relative the first and second axis A1, A2 representative of first and second input values V1, V2 within the primary operational area.

As illustrated in FIG. 3, the method 100 may further comprise:

displaying 113 the visual output 11 on the graphical user interface 9 such that the area 13 comprises at least a second sub-area c2, using the control unit 7, wherein the second sub-area c2 represents a secondary operational area comprising portions at positions relative the first and the second axis A1, A2 representative the first and second input values V1, V2 within the secondary operational area.

As illustrated in FIG. 3, the method 100 may further comprise:

preventing 121 unintended selection of portions within the second sub-area c2 by outputting a notification if a portion is selected within the second sub-area c2, using the control unit 7.

As illustrated in FIG. 3, the method 100 may further comprise:

preventing 122 unintended selection of portions within the second sub-area c2 by requiring an additional control manoeuvre, i.e. an override, to be performed on the input unit 9.1 to allow a selection of a portion within the second sub-area c2, using the control unit 7.

As illustrated in FIG. 3, the method 100 may further comprise:

determining 112 the second sub-area c2 on the basis of individual properties and/or characteristics of a patient 17.

As illustrated in FIG. 3, the method 100 may further comprise:

displaying 114 a symbol 19 on the graphical user interface 9, using the control unit 7, in the area 13 at a position relative the first and second axis A1, A2 representative of a current first input value V1 and current second input value V2 used to control operation of the breathing apparatus 1.

As illustrated in FIG. 3, the method 100 may further comprise:

providing 123 selection of the portion 15 of the area 13 by allowing a user to perform a drag and drop control operation of the symbol 19 in the area 13, using the input unit 9.1.

Figure 4:
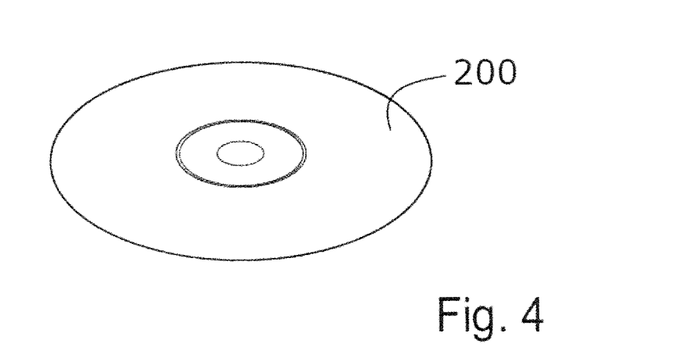
FIG. 4 illustrates a computer program product for performing a method of controlling operation of a breathing apparatus.

FIG. 4 illustrates a computer program product 200 for performing a method of controlling operation of a breathing apparatus 1. The computer program product 200 comprises computer readable code, preferably embedded in the control unit 7, and configured to cause the control unit 7, as illustrated in FIG. 1 or FIG. 2, to perform the method 100 as illustrated in FIG. 3.

Further, the computer program product 200 comprises a computer program for performing a method of controlling operation of a breathing apparatus 1. The computer program comprises computer readable code, preferably embedded in the control unit 7, and configured to cause the control unit 7, as illustrated in FIG. 1 or FIG. 2, to perform the method 100 as illustrated in FIG. 3.

One skilled in the art will appreciate that the method of controlling operation of a breathing apparatus 1 may be implemented by programmed instructions. These programmed instructions are typically constituted by a computer program, which, when it is executed by control unit 7, ensures that the control unit 7 carries out the desired control, such as the method steps described herein. The computer program is usually an embedded part of the computer programme product 200, which comprises a suitable digital storage medium on which the computer program is stored.

The control unit 7 may comprise a calculation unit which may take the form of substantially any suitable type of processor circuit or microcomputer, e.g., a circuit for digital signal processing (digital signal processor, DSP), a Central Processing Unit (CPU), a processing unit, a processing circuit, a processor, an Application Specific Integrated Circuit (ASIC), a microprocessor, or other processing logic that may interpret and execute instructions. The herein utilised expression "calculation unit" may represent a processing circuitry comprising a plurality of processing circuits, such as, e.g., any, some or all of the ones mentioned above. The control unit 7 may further comprise a memory unit, wherein the calculation unit may be connected to the memory unit, which may provide the calculation unit with, for example, stored programme code and/or stored data which the calculation unit may need to enable it to do calculations. The calculation unit may also be adapted to store partial or final results of calculations in the memory unit. The memory unit may comprise a physical device utilised to store data or programs, i.e., sequences of instructions, on a temporary or permanent basis. According to some embodiments, the memory unit may comprise integrated circuits comprising silicon-based transistors. The memory unit may comprise e.g. a memory card, a flash memory, a USB memory, a hard disc, or another similar volatile or non-volatile storage unit for storing data such as e.g. ROM (Read-Only Memory), PROM (Programmable Read-Only Memory), EPROM (Erasable PROM), EEPROM (Electrically Erasable PROM), etc. in different embodiments.

The control unit 7 is connected to components of the breathing apparatus for receiving and/or sending input and output signals. These input and output signals may comprise waveforms, pulses or other attributes which the input signal receiving devices can detect as information and which can be converted to signals processable by the control unit 7. These signals may then be supplied to the calculation unit. Each of the connections to the respective components of the breathing apparatus 1 for receiving and sending input and output signals may take the form of one or more from among a cable, a data bus, e.g. a CAN (controller area network) bus, a MOST (media orientated systems transport) bus or some other bus configuration, or a wireless connection.

In the embodiments illustrated, the breathing apparatus 1 comprises a control unit 7 but might alternatively be implemented wholly or partly in two or more control units that operate together or independently.

The computer program product 200 may be provided for instance in the form of a data carrier carrying computer program code for performing at least some of the steps according to some embodiments when being loaded into one or more calculation units of the control unit 7. The data carrier may be, e.g. a CD ROM disc, as is illustrated in FIG. 4, or a ROM (read-only memory), a PROM (programable read-only memory), an EPROM (erasable PROM), a flash memory, an EEPROM (electrically erasable PROM), a hard disc, a memory stick, an optical storage device, a magnetic storage device or any other appropriate medium such as a disk or tape that may hold machine readable data in a non-transitory manner. The computer program product may furthermore be provided as computer program code on a server and may be downloaded to the control unit 7 remotely, e.g., over an Internet or an intranet connection, or via other wired or wireless communication systems.

It is to be understood that the foregoing is illustrative of various example embodiments and that the invention is defined only by the appended claims. A person skilled in the art will realize that the example embodiments may be modified, and that different features of the example embodiments may be combined to create embodiments other than those described herein, without departing from the scope of the present invention, as defined by the appended claims.

For instance, a portion 15 of the area 13, as referred to above, may encompass a point of the area. In such embodiments, the control unit 7 is configured to set the first input value V1 in response to the position of the selected point relative the first axis A1, and to set the second input value V2 in response to the position of the selected point relative the second axis A2. According to further embodiments, a portion 15 of the area 13, as referred to above, may encompass a portion having a certain size relative the first axis A1 and/or the second axis A2. In such embodiments, the control unit 7 may control operation of the breathing apparatus 1 based on first and second input values V1, V2 within the portion 15 of the area 13.

In all embodiments of above, the control unit 7 may be configured to display explanatory text in the visual output 11 on the graphical user interface 9 for example at the first axis A1 and the second axis A2, indicating the control features of the first input value V1 and the second input value V2.

As used herein, the term "comprising" or "comprises" is open-ended, and includes one or more stated features, elements, steps, components or functions but does not preclude the presence or addition of one or more other features, elements, steps, components, functions or groups thereof.

The invention claimed is:

1. A breathing apparatus, comprising:
   a breathing circuit provided with a patient interface, the breathing circuit being configured to provide an inspiratory patient gas mixture to the patient interface;
   a control unit configured to control operation of the breathing apparatus based on at least a first input value and a second input value;
   a graphical user interface connected to the control unit, wherein the control unit is configured to display a visual output on the graphical user interface comprising an area defined by a first axis and a second axis and wherein the first axis represents values of the first input value and the second axis represents values of the second input value, wherein the area comprises at least a first sub-area which represents a primary operational area comprising selectable portions at positions relative the first and second axis representative of first and second input values within the primary operational area; and
   an input unit configured to provide selection of a portion of the area,
   wherein the control unit is configured to set the first input value in response to the position of the selected portion relative the first axis and to set the second input value in response to the position of the selected portion relative the second axis.

2. The breathing apparatus of claim 1, wherein the primary operational area is a preferred operational area.

3. The breathing apparatus of claim 1, wherein the area comprises at least a second sub-area which represents a secondary operational area comprising portions at positions relative the first and the second axis representative of the first and second input values within the secondary operational area.

4. The breathing apparatus of claim 3, wherein the secondary operational area is a non-preferred operational area.

5. The breathing apparatus of claim 3, wherein the control unit is configured to prevent unintended selection of portions within the second sub-area by outputting a notification if a portion is selected within the second sub-area.

6. The breathing apparatus of claim 3, wherein the control unit is configured to prevent unintended selection of portions within the second sub-area by requiring an additional control manoeuvre to be performed on the input unit to allow a selection of a portion within the second sub-area.

7. The breathing apparatus of claim 3, wherein the second sub-area is determined on the basis of individual properties and/or characteristics of a patient.

8. The breathing apparatus of claim 1, wherein the control unit is configured to display a symbol on the graphical user interface in the area at a position relative the first and second axis representative of a current first input value and current second input value used to control operation of the breathing apparatus.

9. The breathing apparatus of claim 8, wherein the input unit is configured to provide selection of the portion of the area by allowing a user to perform a drag and drop control operation of the symbol in the area.

10. The breathing apparatus of claim 1, wherein the graphical user interface and the input unit form part of a touch sensitive screen.

11. The breathing apparatus of claim 1, wherein the breathing apparatus is an anesthetic breathing apparatus.

12. The breathing apparatus of claim 11, wherein the first input value is representative of a concentration of an anesthetic agent and the second input value is representative of a flowrate of patient gas delivered to the patient interface.

13. The breathing apparatus of claim 11, wherein the first input value is representative of a concentration of an anesthetic agent and the second input value is representative of a rate of change of the concentration of the anesthetic agent.

14. The breathing apparatus of claim 1, wherein the control unit is configured to control operation of the breathing apparatus in a high frequency ventilation mode based on at least the first and second input values and wherein the first input value is representative of a respiratory frequency delivered to the patient interface and the second input value is representative a tidal volume of gas delivered to the patient interface.

15. The breathing apparatus of claim 1, wherein the second input value is representative of a rate of change of the first input value.

16. The breathing apparatus of claim 15, wherein the first input value is representative of a concentration of fresh gas.

17. The breathing apparatus of claim 1, wherein the first input value is independent from the second input value.

18. A method for controlling operation of a breathing apparatus which includes a breathing circuit provided with a patient interface, the breathing circuit being configured to provide an inspiratory patient gas mixture to the patient interface, the breathing apparatus further including a control unit, a graphical user interface connected to the control unit, and an input unit, wherein the method comprises:
   displaying, using the control unit, a visual output on the graphical user interface comprising an area defined by a first axis and a second axis, wherein the first axis represents values of a first input value and the second axis represents values of a second input value;
   displaying, using the control unit, the visual output on the graphical user interface such that the area comprises at least a first sub-area, wherein the first sub-area represents a primary operational area comprising selectable portions at positions relative the first and second axis representative of first and second input values within the primary operational area;
   selecting, using the input unit, a portion of the area;
   setting the first input value in response to the position of the selected portion relative the first axis;
   setting the second input value in response to a position of the selected portion relative the second axis; and
   controlling, using the control unit, an operation of the breathing apparatus based on the first input value and the second input value.

19. The method of claim 18, further comprising:
   displaying, using the control unit, the visual output on the graphical user interface such that the area comprises at least a second sub-area,
   wherein the second sub-area represents a secondary operational area comprising portions at positions relative the first and the second axis representative the first and second input values within the secondary operational area.

20. The method of claim 19, further comprising:
   preventing, using the control unit, an unintended selection of portions within the second sub-area by outputting a notification if a portion is selected within the second sub-area.

21. The method of claim 19, further comprising:
   preventing, using the control unit, unintended selection of portions within the second sub-area by requiring an additional control manoeuvre to be performed on the input unit to allow a selection of a portion within the second sub-area.

22. The method of claim 19, further comprising:
determining the second sub-area on the basis of individual properties and/or characteristics of a patient.

23. The method of claim 18, further comprising:
displaying, using the control unit, a symbol on the graphical user interface in the area at a position relative the first and second axis representative of a current first input value and current second input value used to control operation of the breathing apparatus.

24. The method of claim 18, further comprising:
providing, using the input unit, selection of the portion of the area by allowing a user to perform a drag and drop control operation of the symbol in the area.

25. A computer program for performing a method for controlling operation of a breathing apparatus, wherein the computer program comprises non-transitory computer readable code embedded in a control unit of the breathing apparatus and configured to cause the control unit to operate the breathing apparatus so as to perform the steps of:
displaying, using the control unit, a visual output on the graphical user interface comprising an area defined by a first axis and a second axis, wherein the first axis represents values of a first input value and the second axis represents values of a second input value;
displaying, using the control unit, the visual output on the graphical user interface such that the area comprises at least a first sub-area, wherein the first sub-area represents a primary operational area comprising selectable portions at positions relative the first and second axis representative of first and second input values within the primary operational area;
selecting, using the input unit, a portion of the area;
setting the first input value in response to the position of the selected portion relative the first axis;
setting the second input value in response to a position of the selected portion relative the second axis; and
controlling, using the control unit, an operation of the breathing apparatus based on the first input value and the second input value.

26. A computer program product for performing a method for controlling operation of a breathing apparatus, wherein the computer program product comprises non-transitory computer readable code embedded in a control unit of the breathing apparatus and configured to cause the control unit to operate the breathing apparatus so as to perform the steps of:
displaying, using the control unit, a visual output on the graphical user interface comprising an area defined by a first axis and a second axis, wherein the first axis represents values of a first input value and the second axis represents values of a second input value;
displaying, using the control unit, the visual output on the graphical user interface such that the area comprises at least a first sub-area, wherein the first sub-area represents a primary operational area comprising selectable portions at positions relative the first and second axis representative of first and second input values within the primary operational area;
selecting, using the input unit, a portion of the area;
setting the first input value in response to the position of the selected portion relative the first axis;
setting the second input value in response to a position of the selected portion relative the second axis; and
controlling, using the control unit, an operation of the breathing apparatus based on the first input value and the second input value.

* * * * *